United States Patent [19]

Broughton et al.

[11] Patent Number: 5,399,748
[45] Date of Patent: Mar. 21, 1995

[54] DERIVATIVES OF ASPARTIC ACID AND GLUTAMIC ACID HAVING ANTICHOLECYSTOKININ ACTIVITY

[75] Inventors: Howard B. Broughton, London; Sarkis B. Kalindjian, Banstead; Caroline M. R. Low, Croydon; Iain M. McDonald, Paddock Wood; Robert A. D. Hull, Tonbridge; Nigel P. Shankley, Nr Edenbridge, all of United Kingdom

[73] Assignee: James Black Foundation Limited, Dulwich, United Kingdom

[21] Appl. No.: 961,722

[22] PCT Filed: Jul. 8, 1991

[86] PCT No.: PCT/GB91/01111
  § 371 Date: Jan. 12, 1993
  § 102(e) Date: Jan. 12, 1993

[87] PCT Pub. No.: WO92/00958
  PCT Pub. Date: Jan. 23, 1992

[30] Foreign Application Priority Data
  Jul. 12, 1990 [GB] United Kingdom ............ 9015360
  Dec. 17, 1990 [GB] United Kingdom ............ 9027283

[51] Int. Cl.$^6$ .................................... C07C 311/37
[52] U.S. Cl. .................... 562/427; 514/381; 514/510; 514/533; 514/539; 514/562; 546/176; 548/252; 549/253; 560/10; 560/13; 562/428; 562/430
[58] Field of Search ............ 574/381, 510, 533, 539, 574/562; 560/10, 13; 562/427, 428, 430; 546/176; 548/252; 549/253

[56] References Cited

U.S. PATENT DOCUMENTS

| | | | |
|---|---|---|---|
| 4,018,915 | 4/1977 | Okamoto et al. | 560/13 X |
| 4,791,215 | 12/1988 | Rovati et al. | 562/433 X |
| 4,971,978 | 11/1990 | Nadzan et al. | 514/312 |
| 5,202,344 | 4/1993 | Becker et al. | 514/423 |

FOREIGN PATENT DOCUMENTS 0250148 12/1987 European Pat. Off. .
0272228 6/1988 European Pat. Off. .
PCT/EP91/-
  02342 6/1992 WIPO .

Primary Examiner—José G. Dees
Assistant Examiner—B. Frazier
Attorney, Agent, or Firm—Foley & Lardner

[57] ABSTRACT

Arylsulfonamide derivatives of α-amino dicarboxylic acids such as aspartic acid and glutamic acid posses anti-cholecystokinin activity. They are useful in the treatment of cholecystokinin-related disorders such as anorexia nervosa, pancreatic inflammation, biliary tract disease, Zollinger-Ellison syndrome and various psychiatric disorders, as well as in the potentiation of opiate analgesia, and in the treatment of certain cancers.

12 Claims, No Drawings

DERIVATIVES OF ASPARTIC ACID AND GLUTAMIC ACID HAVING ANTICHOLECYSTOKININ ACTIVITY

This invention relates to amino acid derivatives, and more particularly to amino acid derivatives which possess anti-cholecystokinin activity. The invention also relates to methods for preparing such cholecystokinin antagonists and to compounds which are useful as intermediates in such methods.

Cholecystokinins are peptides which have been found both in gastrointestinal tissue and in the central nervous system. Natural cholecystokinin is a 33 amino acid peptide (CCK-33), the C-terminal 5 amino acids of which are identical to those of gastrin and caerulein. Also found naturally is the C-terminal octapeptide (CCK-8) of CCK-33.

The cholecystokinins are believed to be important in the regulation of appetite. They stimulate intestinal motility, gall bladder contraction, pancreatic enzyme secretion, and are known to have a trophic action. They also inhibit gastric emptying and have various effects in the CNS.

A classification scheme for cholecystokinin receptors has recently been proposed in which the receptors coupled to contraction of the gall bladder and pancreatic secretion are termed CCK-A, while those found in the cerebral cortex are termed CCK-B.

A number of cholecystokinin-receptor antagonists have been reported in the literature. Possible therapeutic uses for CCK-A antagonists include the control of appetite disorders such as anorexia nervosa, and the treatment of pancreatic inflammation, biliary tract disease, Zollinger-Ellison syndrome and various psychiatric disorders. Other possible uses are in the potentiation of opiate (e.g. morphine) analgesia, and in the treatment of cancers. WO 89/02431 discloses a class of glutamic acid and aspartic acid derivatives which are said to be cholecystokinin antagonists. The compounds are of the general formula

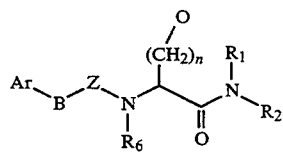

in which Ar is a heterocyclic group, and B may be a bond. Included in the definitions of Z, $R_6$, n, D, $R_1$ and $R_2$ are that Z is —S(O)$_2$—, $R_6$ is H, n is 1 to 3, D is —CO$_2$H, $R_1$ is H and $R_2$ is phenethyl or substituted phenethyl.

The present invention is based on the surprising finding that the group Ar in the above formula may be 2-naphthyl or certain analogues of 2-naphthyl, although the corresponding 1-naphthyl derivatives are inactive. According to the present invention, therefore, there are provided compounds of the formula

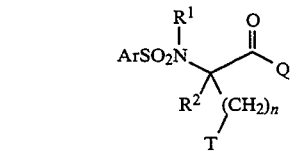

wherein
Ar is

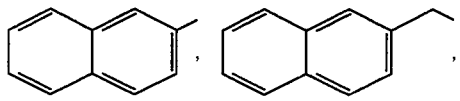

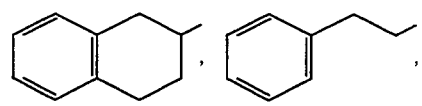

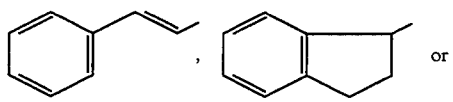

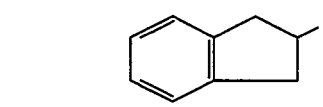

(wherein the aromatic moiety may be substituted or unsubstituted), or

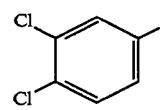

$R^1$ is H, $C_1$ to $C_6$ alkyl, $C_1$ to $C_6$ alkenyl, cycloalkyl, —(CH$_2$)$_q$aryl, —(CH$_2$)$_q$(substituted aryl) or —(CH$_2$)$_q$heterocyclic, wherein q is 0 to 4,
$R^2$ is H, methyl or ethyl,
T is carboxyl, —CONR$^5$R$^6$ (wherein R$^5$ and R$^6$ are independently H or $C_1$ to $C_4$ alkyl) or tetrazolyl,
n is 0 to 3, and
Q is

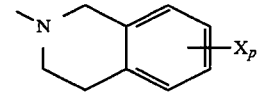

or

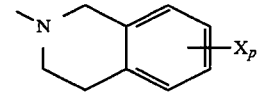

wherein
X is $C_1$ to $C_4$ alkyl, $C_1$ to $C_4$ alkoxy, $C_1$ to $C_4$ thioalkoxy, carboxy, $C_1$ to $C_4$ carboalkoxy, nitro, trihalomethyl, hydroxy, —NR$^7$R$^8$ (wherein R$^7$ and R$^8$ are independently H or $C_1$ to $C_4$ alkyl), $C_1$ to $C_4$ alkylaryl, $C_1$ to $C_4$ alkyl (substituted aryl) or halo,
m is 1 to 3,
p is 0 to 3; and $R^3$ is H, $C_1$ to $C_5$ alkyl or —$(CH_2)_rR^4$ wherein r is 0 to 4 and $R^4$ is aryl or substituted aryl; and pharmaceutically acceptable salts thereof.

Pharmaceutically acceptable salts of the acidic compounds of the invention include salts with alkali metals and alkaline earth metals, such as sodium, potassium, calcium and magnesium, and salts with organic bases. Suitable organic bases include amines such as N-methyl-D-glucamine.

Pharmaceutically acceptable salts of the basic compounds of the invention include salts derived from organic or inorganic acids. Suitable acids include hydrochloric acid, phosphoric acid, oxalic acid, maleic acid, succinic acid and citric acid.

When Ar is a substituted group (other than 3,4-dichlorophenyl), substituents will generally be up to three in number, and may be at any position in the aromatic ring system. Preferably, Ar is unsubstituted 2-naphthyl or mono- or di-substituted 2-naphthyl, but perhalo-substituted compounds are also within the scope of the invention. Suitable substituents other than halo include $C_1$ to $C_4$ alkyl, $C_1$ to $C_4$ alkoxy, sulphonamide, trihalomethyl, nitro, carboxylate and nitrile.

When $R^1$ is —$(CH_2)_q$(substituted aryl), the aryl group may be substituted with one, two or three substituents, independently selected from $C_1$ to $C_4$ alkyl, $C_1$ to $C_4$ alkoxy, $C_1$ to $C_4$ thioalkoxy, carboxy, $C_1$ to $C_4$ carboalkoxy, nitro, trihalomethyl, hydroxy and —$NR^9R^{10}$ (wherein $R^9$ and $R^{10}$ are independently H or $C_1$ to $C_4$ alkyl).

Similarly, when $R^4$ is substituted aryl, or X is $C_1$ to $C_4$ alkyl(substituted aryl), the substituents may be up to three in number, and may be any of those just recited for $R^1$.

The term "aryl", as used herein, includes (but is not limited to) phenyl, naphthyl, indanyl, fluorenyl, (1,2,3,4)tetrahydronaphthyl, indenyl and isoindenyl groups.

The compounds of the invention have a chiral centre at the carbon atom to which $R^2$ is attached. The present invention comprehends both the L- and the D- isomers of the compounds of formula I, as well as racemic mixtures thereof.

Particularly preferred compounds according to the invention are 2-naphthalenesulphonyl-aspartyl (2-phenethyl)amide, 2-naphthalenesulphonyl-glutamyl (2-phenethyl)amide, 2-naphthalenesulphonyl-aspartyl (3-phenylpropionyl)amide, derivatives thereof in which the phenyl group is mono-substituted with a chloro or methoxy group, and the pharmaceutically acceptable salts of such compounds. Especially preferred are the L-isomers of these compounds.

The compounds of the invention in which T is a carboxyl or amido group may be prepared as shown in reaction scheme A. It will be noted that the reaction scheme illustrates the preparation of compounds in the L configuration, but exactly analogous methods are applicable to the preparation of the D or DL compounds.

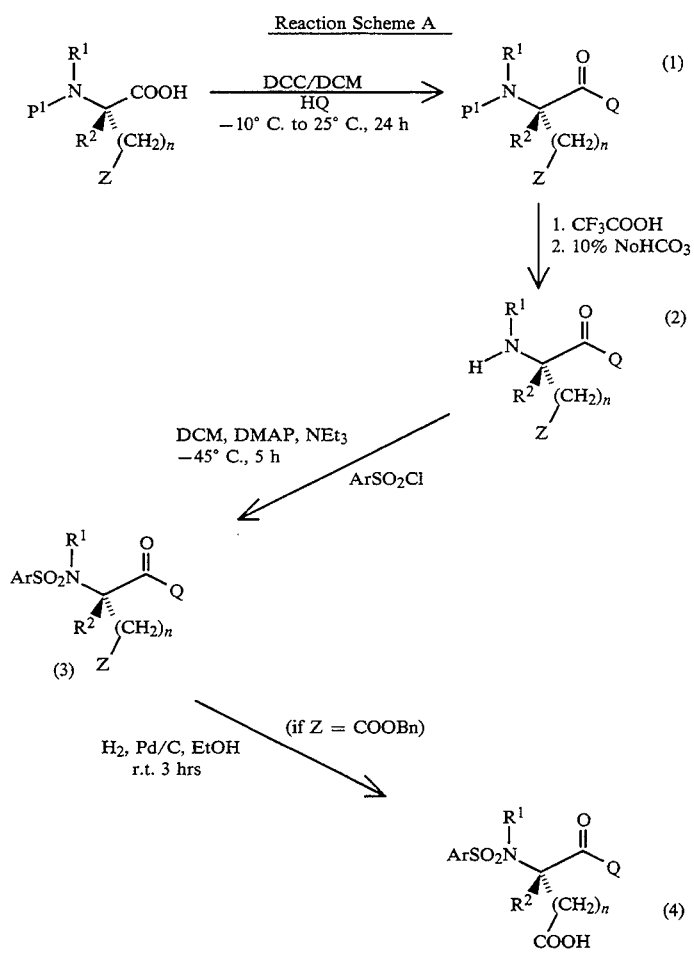

In reaction Scheme A, $R^1$, $R^2$, $R^3$, m, n, X and p have the meanings indicated above in relation to Formula I, while $p^1$ indicates an N-protecting group such as a t-butyloxycarbonyl, benzyloxycarbonyl, sulphonyl, acetyl, pivaloyl or aminoacyl group, and Z is a suitably protected carboxyl group or an amido group.

The first reaction in the scheme involves coupling an N-protected amino acid ester (such as an alkyl, benzyl or substituted benzyl ester) with a primary or secondary amine using a suitable peptide coupling reagent such as dicyclohexylcarbodiimide (DCC), bis(2-oxo-3-oxazolidinyl)phosphinic chloride, isobutyl chloroformate or phosphorus pentachloride. The reaction conveniently takes place at a temperature of from $-10°$ C. to $25°$ C. in a suitable solvent such as dichloromethane. The protecting group $P^1$ is removed from the resulting amide (1) by standard methods. For example, if $P^1$ is a t-butyloxycarbonyl group, trifluoroacetic acid may conveniently be used, followed by neutralisation with sodium bicarbonate, to yield the corresponding amine (2). This is then reacted with the desired 2-naphthyl sulphonyl chloride in the presence of a base (preferably a tertiary amine such as triethylamine) and DMAP, to yield the sulphonamide (3).

If $n\neq 0$ and Z is a protected carboxyl group, it is then deprotected by suitable methods, to give the free acid form (4). When Z is a carboxyl group which is protected by means of its benzyl ester, it may conveniently be deprotected by catalytic hydrogenation (e.g. over Pd/C), but it will be apparent that other methods could also be used.

When $n=0$, Z is 2-furanyl which on ozonolysis and hydrogen peroxide work-up unmasks the free carboxylate of (4).

Those compounds of formula I in which T is tetrazolyl may be made as shown in the following Reaction Scheme B.

Reaction Scheme B

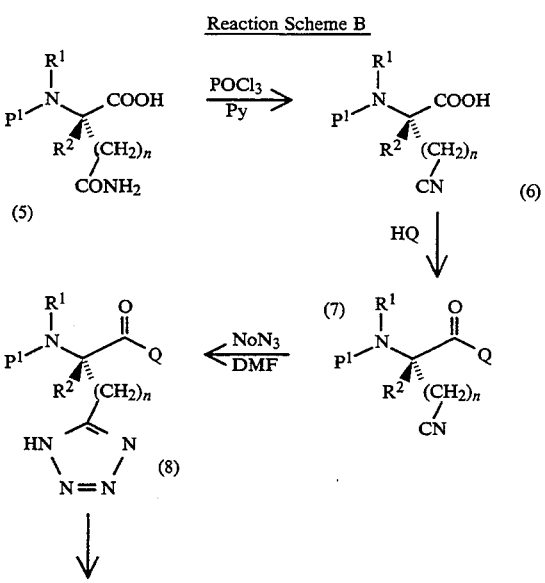

-continued
Reaction Scheme B

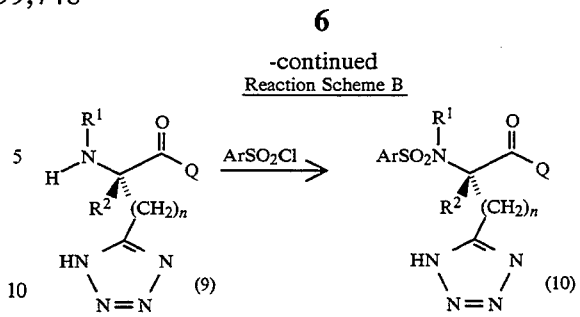

In this scheme, the N-protected asparagine analogue (5) is converted to the corresponding nitrile (6) by reaction with, for example, phosphorus oxychloride and pyridine. This is then coupled with the desired primary or secondary amine, using any of the coupling agents mentioned above, to yield compound (7). The latter is then converted to the tetrazole (8) by reaction with sodium azide in dimethylformamide, followed by deprotection of the amino-nitrogen using standard methods. The product (9) is finally reacted with the appropriate 2-naphthylsulphonyl chloride to give the desired compound (10).

An alternative method for the synthesis of certain compounds according to the invention is shown below in reaction scheme C.

Reaction Scheme C

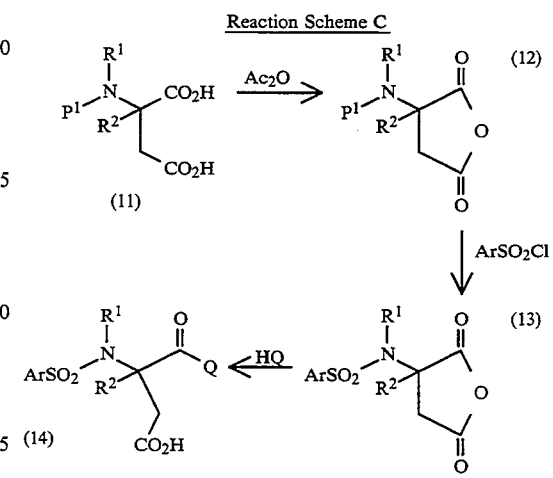

The N-protected amino acid (11) is reacted with a dehydrating agent such as acetic anhydride to form (12), which is deprotected and reacted with the appropriate 2-naphthyl sulphonyl chloride under the usual conditions to give the corresponding sulphonamide (13). Reaction with a primary or secondary amine affords the desired compound (14).

Pharmaceutically acceptable salts of the acid or basic compounds of the invention can of course be made by conventional procedures, such as by reacting the free base or acid with at least a stoichiometric amount of the desired salt-forming acid or base.

The compounds of the invention can be administered by oral or parenteral routes, including intravenous, intramuscular, intraperitoneal, subcutaneous, rectal and topical administration.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride.

Aqueous suspensions according to the invention may include suspending agents such as cellulose derivatives, sodium alginate, polyvinyl-pyrrolidone and gum tragacanth, and a wetting agent such as lecithin.

Suitable preservatives for aqueous suspensions include ethyl and n-propyl p-hydroxybenzoate.

The invention is now further illustrated by means of the following examples.

EXAMPLE 1 a) N-tert-Butyloxycarbonyl β-benzyl-L-aspartyl (2-phenethyl)amide. (1-1)

2-Phenethylamine (4.34 ml; 34.6 mmol) was added to DCC (7.23 g; 35 mmol) and N-tert-butyloxycarbonyl-L-aspartic acid 4-benzyl ester (11.19 g; 34.6 mmol) in dry dichloromethane (230 ml) at $-10°$ C. under argon. The mixture was allowed to warm to 4° C. and stirred for 24 hours. The reaction mixture was filtered, evaporated to dryness, dissolved in ethyl acetate (150 ml), filtered and evaporated, yielding a yellow solid. Trituration with anhydrous ether afforded the product as a white amorphous solid which was filtered and dried in vacuo.

yield (13.45 g; 91%) m.pt. 103° C. I.R. $\nu_{max}$(nujol) 3350, 3322, 1733, 1686, 1654 cm$^{-1}$. NMR $\delta_H$(300 MHz; DMSO-d$^6$) 1.4(9H, s, ((CH$_3$)$_3$C—) 2.6(2H, ddx2, —CH$_2$CO$_2$Bn) 2.7(2H, m, —CH$_2$CH$_2$Ph) 3.3(2H, m, —CONHCH$_2$—) 4.3(1H, m, —HN(CHR)CO—) 5.1(2H, s, —CO$_2$CH$_2$Ph) 7.1 (1H, d, BocHN— exch. D$_2$O) 7.2–7.4(10H, m, -Ph-H) 7.9(1H, t, —CONHCH$_2$— exch. D$_2$O) $[\alpha]_D = -15.2°$ (c=0.79%, MeOH) R$_f$ 0.55 (1:5 acetone-toluene)

b) β-Benzyl-L-aspartyl (2-phenethyl)amide. (1-2)

N-tert-Butyloxycarbonyl β-benzyl-L-aspartyl (2-phenethyl)amide (1-1), (11.55 g; 27 mmol) was dissolved in trifluoroacetic acid (100 ml) and stirred at room temperature for 2 hours. The reaction mixture was evaporated to dryness and the resultant oil dissolved in dichloromethane (150 ml), washed successively with 10% sodium bicarbonate solution (100 ml×2), brine (150 ml×3) and dried (Na$_2$SO$_4$). Filtration and evaporation of the solvent gave the crude product as a yellow oil which solidified on standing. The product was used without further purification.

Yield (8.38 g; 93%) m.pt. 48°–52° C. NMR $\delta_H$(300 MHz; DMSO-d$^6$) 2.0(2H, s, H$_2$N(CHR)CO) 2.6(2H, dd x 2, —CH$_2$CO$_2$Bn) 2.8 (2H, t, —CH$_2$CH$_2$Ph) 3.3 (2H, m, —CONHCH$_2$—) 3.5(1H, dd, H$_2$N(CHR)CO—) 5.1(2H, s, —CO$_2$CH$_2$Ph) 7.1–7.4(10H, m, -Ph-H) 8.0(1H, t, —CONHCH$_2$— exch. D$_2$O) IR $\nu_{max}$(nujol) 3316, 3282, 1721, 1637cm$^{-1}$. $[\alpha]_D = -4.4°$ (C=0.67%, MeOH)

c) 2-Naphthalenesulphonyl-β-benzyl-L-aspartyl (2-phenethyl)amide. (1-3)

2-Naphthalenesulphonyl chloride (641 mg; 2.83 mmol) in dry dichloromethane(10 ml) was added to a solution of β-benzyl-L-aspartyl (2-phenethyl)amide (1-2),(866 mg; 2.65 mmol), triethylamine(0.37 ml;2.65 mmol) and DMAP(22 mg) in dry DCM (40 ml) at $-45°$ C. under argon. The reaction mixture was stirred at $-45°$ C. for a further 5 hours then washed with water (50 ml×2) and dried (Na$_2$SO$_4$). Filtration and evaporation of the solvent gave the crude product as an oily solid. The purified product was obtained by flash chromatography on silica gel with acetone-toluene (1:20 to 1:10) as eluent.

Yield (1.1 g; 80%) m.pt 128° C. I.R. $\nu_{max}$(nujol) 3375, 1739, 1662, 1177, 1162 cm$^{-1}$. NMR $\delta_H$(300 MHz; DMSO-d$^6$) 2.3 (2H,t,CH$_2$CH$_2$Ph) 2.4(2H,m,—CH$_2$CO$_2$Bn) 2.8(2H,m,—CONHCH$_2$—) 4.2(1H,q,—NH(CHR)CO—) 4.9(2H,dd,—CO$_2$CH$_2$Ph) 6.9(2H,d,—Ar—H) 7.1–7.4(8H,m,—Ar—H) 7.6 (2H,m, —Ar—H) 7.7(1H,d,—Ar—H) 8.0(4H,m,—Ar—H and —NH—exch. D$_2$O) 8.4(1H,s,—Ar—H) $[\alpha]_D = -12.2°$ (c=0.74%, MeOH) R$_f$ 0.42(1:10 acetone-toluene)

d) 2-Naphthalenesulphonyl-L-aspartyl (2-phenethyl)amide (1-4)

2-Naphthalenesulphonyl β-benzyl-L-aspartyl (2-phenethyl)amide (1-3), (228 mg; 0.44 mmol) in ethanol (40 ml), was stirred at room temperature with 10% palladium on charcoal (38 mg) under an atmosphere of hydrogen. After 3 hours, hydrogen was no longer being consumed and the reaction mixture was filtered through a pad of celite. Evaporation of the solvent gave the crude product as a clear solid. Trituration with anhydrous ether afforded a white amorphous solid which was filtered and dried in vacuo.

yield (165 mg; 92%) m.pt. 184°–185.5° C. IR $\nu_{max}$(nujol) 3373, 3249, 1654, 1550, 1341, 1166cm$^{-1}$. NMR $\delta_H$(300 MHz; DMSO-d$^6$) 2.2–2.4(4H, m, —CH$_2$CO$_2$H and —CH$_2$CH$_2$Ph) 2.8(2H, m, —CONHCH$_2$—) 4.0(1H, t, —NH(CHR)CO—) 6.9 and 7.2(5H, m, -Ph-H) 7.6(2H, m, —Ar—H $^{5,7}$) 7.7(1H, 2xdd, —Ar—H$^4$) 8.0(5H, m, —Ar—H$^{3,6,8}$ and —NH x 2 exch. D$_2$O) 8.35(1H, s, —Ar—H$^1$)

$\delta_c$(DMSO-d$^6$) 38.98(—CH$_2$CO$_2$H) 42.15(—CH$_2$CH$_2$Ph) 44.71(—CONHCH$_2$—) 57.84(—NH(CHR)CO—) 127.02(-Ph-C$^m$) 130.02, 132.22, 132.30, 132.46, 132.95, 133.05, 133.54, 133.79(-Ph-C$^{o,p}$ and —Ar—C$^{1,3,4,5,6,7,8}$) 136.17, 138.88(—Ar—C$^{1a,4a}$) 141.93, 143.50(—Ar—C$^2$ and -Ph-C) 174.09, 175.82(—CO$_2$H and —COONH—) $[\alpha]_D = -24.8°$ (c=0.48% MeOH)

Found: C 61.68, H 5.21, N 6.46%; C$_{22}$H$_{22}$N$_2$O$_5$S requires C 61.96, H 5.20, N 6.57%. R$_t$ (HPLC) 4.0 min. (C$_8$, 30:70 H$_2$O—CH$_3$CN, +0.1% CH$_3$CO$_2$H)

EXAMPLE 2 (COMPARATIVE)

4-Toluenesulphonyl-β-benzyl-L-aspartyl (2-phenethyl)amide (2-3) was prepared from (1-2) (470 mg; 1.44 mmol) and 4-toluenesulphonyl chloride (307 mg; 1.6 mmol) as described for the preparation of (1-3). The product was obtained as white solid after work-up and chromatography.

Yield (547 mg; 79%) m.pt 84° C. NMR $\delta_H$(300 MHz; DMSO-d6) 2.4(3H, s, —CH$_3$) 2.3-2.6(4H, m, —CH$_2$CO$_2$Bn and —CH$_2$Ph) 3.0(2H, m, —CONHCH$_2$—) 4.1(1H, bs, —NH(CHR)CO—) 4.95(2H, q, —CO$_2$CH$_2$Ph) 7.1-7.4(12H, m, -Ph-H and —Ar—H) 7.6(2H, d, —Ar—H) 8.0(1H,t, —NH—) 8.1(1H, s, —NH—) $[\alpha]_D$= —13.0° (C=0.69%; MeOH)

4-Toluenesulphonyl-L-aspartyl (2-phenethyl)amide (2-4) was obtained on hydrogenolysis of (2-3) (384 mg; 0.8 mmol) as described for the preparation of 2-naphthalenesulphonyl L-aspartyl (2-phenethyl)amide (1-4 ).

Yield (281 mg; 90% ) m.pt. 140°-141° C. NMR $\delta_H$(300 MHz; DMSO-d6) 2.2-2.4(2H, 2xdd, —CH$_2$CO$_2$H) 2.3(3H, s, —CH$_3$) 3.0(2H, t, —CONHCH$_2$—) 4.0(1H, t, —HN(CHR)CO—) 7.1-7.4(7H, m, -Ph-H and —Ar—H) 7.6(2H, d, —Ar—H) 7.95(1H, t, —NH) $[\alpha]_D$= —28.1° (c=0.64%; MeOH) Found c 58.38, H 5.63, N 7.21; C$_{19}$H$_{22}$N$_2$O$_5$S requires C 58.45, H 5.63, N 7.17%.

EXAMPLE 3 (COMPARATIVE)

Benzenesulphonyl-$\beta$-benzyl-L-aspartyl (2-phenethyl)amide (3-3) was prepared from (1-2) (250 mg; 0.76 mmol) and benzenesulphonyl chloride(0.12 ml; 0.94 mmol), as described for the preparation of (1-3). The product was obtained as a white solid after work-up and chromatography.

Yield (322 mg; 90%) NMR $\delta$ (300 MHz; CDCl$_3$) 2.3 and 3.1 (2H, 2xdd, —CH$_2$CO$_2$Bn) 2.7(2H, t, —CH$_2$Ph) 3.4(2H, m, —CONHCH$_2$—) 4.0(1H, m, —NH(CHR)CO—) 5.1(2H, q, —CO$_2$CH$_2$Ph) 6.0(1H, d, —SO$_2$NH—) 6.7(1H, t, —CONH—) 7.2-7.8(15H, m, -Ph-H)

Benzenesulphonl-L-aspartyl (2-phenethyl)amide (3-4) was obtained on hydrogenolysis of (3-3) (322 mg; 0.75 mmol) as described for the preparation of 2-naphthalenesulphonyl L-aspartyl (2-phenethyl)amide (1-4).

Yield (223 mg; 86%) m.pt. 174°-175° C. NMR $\delta$(300 MHz; DMSO-d6) 2.3(2H, 2xdd, —CH$_2$CO$_2$H) 2.5(2H, m, —CH$_2$Ph) 3.0(2H, m, —CONHCH$_2$—) 4.0(1H, t, —NH(CHR)CO—) 7.1-7.3(5H, m, —CH$_2$Ph-H) 7.5(3H, m, —SO$_2$Ph-H) 7.7(2H, d, —SO$_2$Ph-H) 7.95(1H, t, —CONH—) 8.1(1H, d, —SO$_2$NH—) $[\alpha]_D$= —28.0 (c=1.0%, MeOH) Found C 57.08, H 5.35, N 7.44; C$_{18}$H$_{20}$N$_2$O$_5$S requires C 57.43, H 5.51, N 7.25%.

EXAMPLE 4 (COMPARATIVE)

1-Naphthalenesulphonyl-$\beta$-benzyl-L-aspartyl (2-phenethyl)amide (4-3) was prepared from (1-2) (250 mg; 0.77 mmol) and 1-naphthalenesulphonyl chloride (185 mg; 0.81 mmol), as described for (1-3). The product was obtained in pure form after work-up and chromatography.

Yield (300 mg; 75%) NMR $\delta$(300 MHz; CDCl$_3$) 2.1 and 3.0(2H, 2xdd, —CH$_2$CO$_2$Bn) 2.5(2H, t, —CH$_2$Ph) 3.3(2H, m, —CONHCH$_2$—) 3.9(1H, m, —NH(CHR)CO—) 4.9(2H, q, —CO$_2$CH$_2$Ph) 6.3(1H, d, —SO$_2$NH—) 6.6(1H, t, —CONH—) 7.1-7.4(10H, m, -Ph-H) 7.6(3H, m, —Ar—H) 8.0, 8.1, 8.3, 8.5(4H, 4xd, —Ar—H)

1-Naphthalenesulphonyl-L-aspartyl (2-phenethyl)amide (4-4) was obtained on hydrogenolysis of (4-3) (300 mg; 0.58 mmol) as described for the preparation of 2-naphthalenesulphonyl L-aspartyl (2-phenethyl)amide (1-4).

Yield (140 mg; 57%) m.pt. 205°-206° C. NMR $\delta$(300 MHz; DMSO-d6) 2.3(2H, 2xdd, —CH$_2$CO$_2$H) 2.3(2H, m, —CH$_2$Ph) 2.8(2H, m, —CONHCH$_2$—) 4.0(1H, t, —NH(CHR)CO—) 7.0 and 7.3(5H, m, —CH$_2$Ph—H) 7.6(4H, m, —Ar—H and —CONH—) 7.8(1H, t, —SONH—) 8.0, 8.2, and 8.6(4H, 4xd, —Ar—H) $[\alpha]_D$= —26.0 (c=1.0%, MeOH) Found C 61.89, H 5.17, N 6.43; C$_{22}$H$_{22}$N$_2$O$_5$S requires C 61.96, H 5.20, N 6.57%

The following compounds were synthesised by the method described above for the preparation of 2-Naphthalenesulphonyl-L-aspartyl (2-phenethyl)amide (1-4).

EXAMPLE 5 (COMPARATIVE)

4-Methoxybenzenesulphonyl-L-aspartyl (2-phenethyl)amide m.pt. 132° C. NMR $\delta_H$(300 MHz; DMSO-d6) 2.3(2H, ddx2, —CH$_2$CO$_2$H) 3.05(2H, m, —CH$_2$Ph) 3.30(2H, m, —CONHCH$_2$—) 3.75(3H, s, —OCH$_3$) 3.95(1H, m, —NH(CHR)CO—) 7.0(2H, d, Ar—H$^3$) 7.3-7.3(5H, m, Ph-H) 7.7(2H, d, Ar—H$^2$) 7.9(2H, t, —COHN— and —SO$_2$NH—) $[\alpha]_D$= —22.0° (c=1.0%; MeOH) Found C 55.82, H 5.59, N 6.96%; C$_{19}$H$_{22}$N$_2$O$_6$S requires C 56.15, H 5.46, N 6.89%

EXAMPLE 6 (COMPARATIVE)

Phenylmethanesulphonyl-L-aspartyl 2-phenethylamide m.pt. 142° C. NMR $\delta_H$(300 MHz; DMSO-d6) 2.5(2H, m, —CH$_2$CO$_2$H) 2.7(2H, m, —CH$_2$Ph) 3.3(2H, m, —CONHCH$_2$—) 4.15(1H, t, —NH(CHR)CO—) 4.3(2H, q, —CH$_2$SO$_2$N—) 7.2-7.4(10H, m, Ph-H) 7.6(1H, bs, —SO$_2$NH—) 8.1(1H, t, —CONH—) $[\alpha]_D$= —29.0° (c=1.0%; MeOH) Found C 58.32, H 5.77, N 7.09%; C$_{19}$H$_{22}$N$_2$O$_5$S requires C 58.45, H 5.68, N 7.17%:

EXAMPLE 7

2-phenylethanesulphonyl-L-aspartyl (2-phenethyl)amide m.pt 110°-115° C. NMR $\delta_H$(300 MHz; DMSO-d6) 2.5(2H, m, —CH$_2$CH$_2$SO$_2$NH—) 2.64(2H, m, —CH$_2$CO$_2$H) 2.88(2H, m, —CH$_2$Ph) 3.05-3.2(2H, m, —CONHCH$_2$—) 3.2-3.3(2H, m, —CH$_2$SO$_2$NH—) 4.1(1H, m, —NH(CHR)CO—) 7.0-7.4(10H, m, Ph-H) 7.65(1H, s, —SO$_2$NH—) 8.14(1H, t, —CONH—) $[\alpha]_D$= —32.1° (c=0.52%; MeOH)

EXAMPLE 8 (COMPARATIVE)

3-Phenylprophanesulphnyl-L-aspartyl (2-phenethyl)amide NMR $\delta_H$(300 MHz; DMSO-d6) 1.9(2H, m, —CH$_2$CH$_2$SO$_2$NH—) 2.45(2H, m, —CH$_2$CO$_2$H) 2.6(4H, m, 2x—CH$_2$Ph) 2.9(2H, m, —CH$_2$SO$_2$N—) 3.2(2H, m, —CONHCH$_2$—) 4.0(1H, m, —NH(CHR)CO—) 7.1-7.3(10H, m, Ph-H) 7.55(1H, d, —SO$_2$NH—) 8.07(1H, t, —CONH—) $[\alpha]_D$= —35.0° (c=0.2%; MeOH)

EXAMPLE 9

3,4-Dichlorobenzenesulphonyl-L-aspartyl (2-phenethyl)amide m.pt. 169° C. NMR $\delta_H$(300 MHz; DMSO-d6) 2.3(4H, m, —CH$_2$CO$_2$H and —CH$_2$Ph) 3.0(2H, m, —CONHCH$_2$—) 4.0(1H, t, —NH(CHR)CO—) 7.2(5H, m, Ph-H ) 7.7(1H, d, Ar—H$^5$) 7.8(1H, d, Ar—H$^6$) 7.9(1H, s, Ar—H$^2$) 8.2 (1H, t, —CONH—) 8.4(1H, bs, —SO$_2$NH—) $[\alpha]_D$=15.6° (c=1.0%; MeOH) Found C 48.26, H 3.99, N 6.32%; C$_{18}$H$_{18}$Cl$_2$N$_2$O$_5$S requires C 48.55, H 4.07, N 6.29%: R$_t$ (HPLC) 7.0 min. (C$_8$, 45:55 H$_2$O—CH$_3$CN, +0.1% CH$_3$CO$_2$H)

EXAMPLE 10

Naphthylmethanesulphonyl-L-aspartyl (2-phenethyl)amide m.pt. 171°-172° C. NMR $\delta_H$(300 MHz; DMSO-d$^6$) 2.3(2H, m, —CH$_2$CO$_2$H) 2.7(2H, m, —CH$_2$Ph) 3.3(2H, m, —CONHCH$_2$—) 4.16(1H, m, —NH(CHR)CO—) 4.43(2H, m, —CH$_2$SO$_2$NH—) 7.2(5H, m, Ar—H) 7.59 and 7.9(7H, m, Ar—H) 7.60(1H, d, —SO$_2$NH—) 8.06(1H, bs, —CONH—) $[\alpha]_D = -11.02°$ (c=0.59%; DMSO-d$^6$) Found C 62.66, H 5.43, N 6.46%; C$_{23}$H$_{24}$N$_2$O$_5$S requires C 62.71, H 5.49, N 6.36%:

EXAMPLE 11 (COMPARATIVE)

1-Hexadecanesulphonyl-L-aspartyl (2-phenethyl)amide m.pt. 97° C. NMR $\delta_H$(300 MHz, CDCl$_3$) 0.9(3H, t, —CH$_3$) 1.3(24H, bs, —(CH$_2$)$_{14}$—) 1.7(2H, m, —CH$_2$CH$_2$SO$_2$NH—) 2.8(2H, m, —CH$_2$Ph) 2.95(2H, m, —CH$_2$SO$_2$NH—) 2.75 and 3.1(2H, 2xdd, —CH$_2$CO$_2$H) 3.5 (2H, q, —CONHCH$_2$—) 4.2(1H, m, —NH(CHR)CO—) 5.8(1H, d, —SO$_2$NH—) 6.8(1H, t, —CONH—) 7.2-7.3(5H, m, Ph-H) $[\alpha]_D = +2.0°$ (c=1.0%; CH$_2$Cl$_2$) Found C 59.82, H 9.36, N 4.78%; C$_{28}$H$_{48}$N$_2$O$_5$S. 2H$_2$O requires C 59.97, H 9.35, N 5.00%

EXAMPLE 12

6-Methoxynaphthalenesulphonyl-L-aspartyl (2-phenethyl)amide m.pt. 194°-196° C. NMR $\delta_H$(300 MHz; DMSO-d$^6$) 2.2(2H, m, —CH$_2$CO$_2$H) 2.4(2H, m, —CH$_2$Ph) 2.8(2H, m, —CONHCH$_2$—) 3.9(3H, s, —OCH$_3$) 4.05(1H, m, —NH(CHR)CO—) 6.9 and 7.2 (6H, m, Ph-H and —CONH—) 7.25(1H, d, Ar—H$^7$) 7.4) 1H, s, Ar—H$^5$) 7.7(1H, d, Ar—H$^3$) 7.9(2H, m, Ar—H$^{3,8}$) 7.95(1H, bs, —SO$_2$NH— ex. D$_2$O) 8.25(1H, s, Ar—H$^1$) $[\alpha]_D = -16.98°$ (c=0.18%; MeOH) Found C 60.71, H 5.20, N 6.15%; C$_{23}$H$_{24}$N$_2$O$_6$S requires C 60.51, H 5.30, N 6.14%: R$_t$ (HPLC) 7.7 min. (C$_8$, 50:50 H$_2$O—CH$_3$CN, +0.1% CH$_3$CO$_2$H)

EXAMPLE 13

5-Chloro-6-methoxynaphthalenesulphonyl-L-aspartyl (2-phenethyl)amide m.pt. 194°-196° C. NMR $\delta_H$(300 MHz; DMSO-d$^6$) 2.3(2H, m, —CH$_2$CO$_2$H) 2.4(2H, m, —CH$_2$Ph) 2.8(2H, m, —CONHCH$_2$—) 4.0(3H, s, -OCH$_3$) 4.05(1H, m, —NH(CHR)CO—) 6.9 and 7.2(5H, d and m, Ph-H) 7.66(1H, d, Ar—H$^7$) 7.85(1H, d, Ar—H$^3$) 7.95(1H, t, —CONH—) 8.15(2H, d, Ar—H$^{3,8}$) 8.2(1H, bs, —SO$_2$NH—) $[\alpha]_D = -21.74°$ (c=0.23%; MeOH) Found C 55.72, H 5.08, N 6.11%; C$_{23}$H$_{23}$ClN$_2$O$_6$S. 0.25H$_2$O requires C 55.76, H 4.78, N 5.65%: R$_t$ (HPLC) 9.1 min. (C$_8$, 50:50 H$_2$O—CH$_3$CN, +0.1% CH$_3$CO$_2$H)

EXAMPLE 14

5-Chloro-6,7-dimethoxynaphthalenesulphonyl-L-aspartyl (2-phenethyl)amide m.pt. 193°-196° C. NMR $\delta_H$(300 MHz; DMSO-d$^6$) 2.1(2H, m, —CH$_2$CO$_2$H) 2.8(2H, m, —CH$_2$Ph) 3.75(2H, m, —CONHCH$_2$) 3.80(3H, s, —OCH$_3$) 3.92(3H, s, —OCH$_3$) 4.02(1H, m, —NH(CHR)CO—) 7.67(1H, s, Ar—H$^8$) 7.74(1H, d, Ar—H$^4$) 7.7-8.4(1H, bs, —SO$_2$NH—) 7.98(1H, m, —CONH—) 8.11(1H, d, Ar—H$^3$) 8.33(1H, s, Ar—H$^1$) $[\alpha]_D = -28.6°$ (c=0.11%; MeOH) R$_t$(HPLC) 10.7 min. (C$_8$, 50:50 H$_2$O—CH$_3$CN, +0.1% CH$_3$CO$_2$H)

EXAMPLE 15

2-Naphthalenesulphonyl-D-aspartyl (2-phenethyl)amide m.pt. 160°-161° C. NMR $\delta_H$(300 MHz; DMSO-d$^6$) 2.3(2H, m, —CH$_2$Ph) 2.4(2H, 2xdd, —CH$_2$CO$_2$H) 2.8(2H, m, —CONHCH$_2$—) 4.05(1H, t, —NH(CHR)CO—) 6.95 and 7.15(5H, 2xm, Ph-H) 7.6(2H, m, Ar—H$^{5,7}$) 7.8(1H, d, Ar—H$^4$) 8.0(4H, m, Ar—H$^{3,6,8}$ and —CONH—) 8.4(1H, s, Ar—H$^1$) $[\alpha]_D = +20.0°$ (c=0.55%; MeOH) Found C 61.66, H 5.24, N 6.61%; C$_{22}$H$_{22}$N$_2$O$_5$S requires C 61.96, H 5.20, N 6.57%

EXAMPLE 16

2-Naphthalenesulphonyl-L-glutamyl (2-phenethyl)amide m.pt. 212°-215° C. NMR $\delta_H$(300 MHz; DMSO-d$^6$) 1.6(2H, m, —CH$_2$CH$_2$CO$_2$H) 2.0(2H, m, —CH$_2$CO$_2$H) 2.4(2H, t, —CH$_2$Ph) 3.0(2H, m, —CONHCH$_2$—) 3.6(1H, t, —NH(CHR)CO—) 7.0 and 7.2(5H, d and m, Ph-H) 7.6(2H, m, Ar—H$^{5,7}$) 7.8(1H, d, Ar—H$^4$) 7.9(1H, t, —CONH—) 8.0(1H, d, Ar—H$^3$) 8.05(2H m, Ar—H$^{6,8}$) 8.4(1H, s, Ar—H$^1$) $[\alpha]_D = +9.5°$ (c=0.63%; DMF) Found C 62.06, H 5.24, N 6.06%; C$_{23}$H$_{24}$N$_2$O$_5$S. 0.25H$_2$O requires C 62.08, H 5.55, N 6.30%

EXAMPLE 17

-Naphthalenesulphonyl-D-glutamyl (2-phenethyl)amide m.pt. 222°-224° C. NMR $\delta_H$(300 MHz; DMSO-d$^6$) 1.6(2H, m, —CH$_2$CH$_2$CO$_2$H) 2.1(2H, m, —CH$_2$CO$_2$H) 2.3(2H, t, —CH$_2$Ph) 2.8(2H, m, —CONHCH$_2$—) 3.7(1H, m, —NH(CHR)CO—) 7.1(5H, m, Ph-H) 7.6(2H, m, Ar—H$^{5,7}$) 7.8(1H, d, Ar—H$^4$) 7.9(1H, t, —CONH—) 8.0(1H, d, Ar—H$^3$) 8.05(2H, m, Ar—H$^{6,8}$) 8.4(1H, s, Ar—H$^1$) $[\alpha]_D = -21.0°$ (c=0.14%; DMF) Found C 62.34, H 5.58, N 6.60%; C$_{23}$H$_{24}$N$_2$O$_5$S. 0.25H$_2$O requires C 62.08, H 5.55, N 6.30%

EXAMPLE 18

2-Naphthalenesulphonyl-L-aspartyl (2(4-fluorophenethyl)amide) m.pt. 186° C. NMR $\delta_H$(300 MHz; DMSO-d$^6$) 2.3(4H, t and dd, —CH$_2$Ar and —CH$_2$CO$_2$H) 2.8(2H, m, —CONHCH$_2$—) 4.05(1H, t, —NH(CHR)CO—) 7.0(4H, d, Ar—H) 7.6(2H, m, Ar—H$^{5,7}$) 7.75(1H, d, Ar—H$^4$) 8.0 (4H, m, Ar—H$^{3,6,8}$ and —CONH—) 8.4(1H, s, Ar—H$^1$) $[\alpha]_D = -26.7°$ (c=0.6%; MeOH) Found C 59.34, H 4.72, N 6.49%; C$_{22}$H$_{21}$FN$_2$O$_5$S requires C 59.45, H 4.76, N 6.30%

EXAMPLE 19

Naphthalenesulphonyl-L-aspartyl (2-(4-methoxyphenethyl)amide) m.pt. 183°-184° C. NMR $\delta_H$(300 MHz; DMSO-d$^6$) 2.2(2H, t, —CH$_2$Ar) 2.3(2H, 2xdd, —CH$_2$CO$_2$H) 2.8(2H, m, —CONHCH$_2$—) 3.7(3H, s, —OCH$_3$) 4.1(1H, t, —NH(CHR)CO—) 6.75(2H, d, Ar—H$^m$) 6.85(2H, d, Ar—H$^o$) 7.6(2H, m, Ar—H$^{5,7}$) 7.8(1H, d, Ar—H$^4$) 7.9(1H, t, —CONH—) 8.0(4H, m, Ar—H$^{3,6,8}$ and —SONH—) 8.4(1H, s, Ar—H$^1$) $[\alpha]_D = -20.5°$ (c=0.78%; MeOH) Found C 60.59, H 5.12, N 6.05%; C$_{23}$H$_{24}$N$_2$O$_6$S requires C 60.51, H 5.30, N 6.14%

EXAMPLE 20

2-Naphthalenesulphonyl-L-aspartyl (2-(4-sulphonamidophenethyl)amide) m.pt. 181° C. NMR $\delta_H$(300 MHz; DMSO-d$^6$) 2.3(4H, m, —CH$_2$Ar and —CH$_2$CO$_2$H) 2.8(2H, m, —CONHCH$_2$—) 4.0(1H, t, —NH(CHR)CO—) 7.2(2H, d, Ar—H$^o$) 7.3(2H, s, —SO$_2$NH$_2$ ex. D$_2$O) 7.6(4H, d, Ar—H$^m$ and Ar—H$^{5,7}$) 7.8(1H, d, Ar—H$^4$) 8.1(4H, m, Ar—H$^{3,6,8}$ and —CONH—) 8.4(1H, s, Ar—H$^1$) $[\alpha]_D = -25.0°$ (c=0.64%; MeOH) Found C 51.61, H 4.97, N 8.44%; C$_{22}$H$_{23}$N$_3$O$_7$S$_2$. 0.4H$_2$O requires C 51.53, H 4.68, N 8.20%

EXAMPLE 21

2-Naphthalenesulphonyl-L-aspartyl (1,2,3,4-tetrahydroisoquinolin)amide m.pt. 96°–98° C. NMR $\delta_H$(300 MHz; CDCl$_3$) 2.0 and 2.4(2H, 2xm, —CH$_2$CO$_2$H) 2.5(2H, m, —CH$_2$CH$_2$Ar) 3.4(1H, m, —NH(CHR)CO—) 3.6 and 4.8(2H, 2xm, —NCH$_2$CH$_2$Ar) 4.3 and 4.6(2H, d and q, —NCH$_2$—) 6.9(1H, m, —SO$_2$NH—) 7.0–7.2(4H, m, Ar—H) 7.6(2H, 2xm, Ar—H[5,7]) 7.7(1H, d, Ar—H[4]) 7.8(3H, m, Ar—H[3,6,8]) 8.4(1H, 2xs, Ar—H[1]) [α]$_D$= +6.0° (c=1.0%; MeOH) Found C 61.09, H 4.99, N 6.45%; C$_{23}$H$_{22}$N$_2$O$_5$S. 0.67H$_2$O requires C 61.31, H 5.22, N 6.22%

EXAMPLE 22

2-phenethenylsulphonyl-L-aspartyl (2-phenethyl)amide m.pt. 126° C. NMR $\delta_H$(300 MHz; MeOH) 2.6(4H, t, —CH$_2$Ph and —CONHCH$_2$—) 3.3(2H, m, —CONHCH$_2$—) 4.1(1H, t, —NH(CHR)CO—) 7.0(1H, d, PhCHCHSO$_2$—) 7.2(6H, m, Ph-H and PhCHCHSO$_2$—) 7.4(4H, bs, Ph-H and —SO$_2$NH—) 7.6(2H, m, Ph-H) 8.1(1H, t, —CONH—) [α]$^D$=15.10° (c=0.86%; MeOH) Found C 57.2 1, H 5.89%; C$_{20}$H$_{22}$N$_2$O$_5$S. H$_2$O requires C 57.13, H 5.75%

EXAMPLE 23

2-Naphthalenesulphonyl-L-aspartyl (3-phenylpropyl)amide m.pt. 148° C. NMR $\delta_H$(300 MHz; DMSO) 1.4(2H, t, —CH$_2$CH$_2$CH$_2$—) 2.3 (2H, t, —CH$_2$Ph) 2.5(2H, m, —CH$_2$CO$_2$H) 2.6(2H, m, —CONHCH$_2$—) 4.1(1H, t, —NH(CHR)CO—) 7.2(1H, m, Ph-H) 7.6(2H, m, Ar—H[5,7]) 7.8(1H, d, Ar—H[4]) 8.0(4H, m, Ar—H[3,6,8] and —CONH—) 8.2(1H, bs, —SO$_2$NH—) 8.4(1H, s, Ar—H[1]) [α]$^D$=21.70° (c=0.97%, MeOH) Found C 62.58, H 5.52, N 6.51%; C$_{23}$H$_{24}$N$_2$O$_5$S requires C 62.71, H 5.49, N 6.36%

BIOLOGICAL DATA

The compounds were assayed using the CCK-receptor bioassay as follows:

Isolated, strip preparations were prepared from gallbladders removed from male Dunkin-Hartley guinea-pigs (250–500 g body weight) according to the method of La Morte, W. W., et al., J.P.E.T., 217, (3), 638–644 (1981).

The complete gall-bladder is removed and opened along the longitudinal axis. Strips measuring 3 mm in the longitudinal axis and 1 mm in the transverse axis are cut and then tied with cotton to stainless steel wires. The preparation is connected to a GRASS FTO3 isometric transducer under an initial loading tension of 1 g and is immersed in 20 mls of Krebs solution maintained at 37° C. and gassed with 95% O$_2$/5% CO$_2$. The composition (mM) of the Krebs solution is as follows: Na$^+$ 143, K$^+$ 5.9, Ca$^{2+}$ 0.5, Mg$^{2+}$ 1.2, Cl$^-$ 128, H$_2$PO$_4^-$ 2.2, HCO$_3^-$ 24.9, SO$_4^{2-}$ 1.2, dextrose 10. After 30 mins the preparation is washed. Drug addition begins after an initial 90 min stabilisation period. Responses are measured as changes in tension from that immediately prior to any drug addition. Single cumulative agonist concentration-effect curves, using CCK-8 as agonist, are obtained on each preparation in the absence and presence of test compound which has been incubated for 60 minutes. The antagonist activity of the test compound is estimated and expressed as the negative logarithm (base 10) of the equilibrium dissociation constants (pK$_B$) using the modifications of standard competitive analysis described by Black et al., Br. J. Pharmacol.,86,571–579, (1985) and Shankley et al., Br. J. Pharmacol.,94,264–274 (1988). The results are set out in Table 1.

TABLE 1

| Example No. | pK$_B$ versus CCK (gallbladder) |
|---|---|
| 1 | 6.49 ± 0.13 |
| 7 | 5.46 ± 0.16 |
| 9 | 5.77 ± 0.29 |
| 10 | 5.40 ± 0.18 |
| 12 | 6.59 ± 0.21 |
| 13 | 6.49 ± 0.38 |
| 14 | 6.21 ± 0.28 |
| 15 | 5.92 ± 0.32 |
| 16 | 6.14 ± 0.19 |
| 18 | 6.57 ± 0.19 |
| 19 | 5.99 ± 0.34 |
| 20 | 4.95 ± 0.27 |
| 21 | 5.14 ± 0.24 |
| 22 | 6.27 ± 0.22 |
| 23 | 6.98 ± 0.24 |

The compounds of the comparative examples are inactive at CCK-A up to a concentration of 10$^{-5}$M.

Selectivity testing

The compounds were assayed for selectivity using the mouse stomach assay as described by Black, J. W. and Shankley, N. P., Br. J. Pharmacol., 86, 571–579, and also in the guinea-pig fundus assay, as follows:

The stomach is removed from a male Dunkin-Hartley guinea-pig (250–500 g), and Krebs solution is injected through a hypodermic needle under the top stomach muscle layer. The Krebs solution is as detailed above in connection with the gallbladder assay, except that the Ca$^{2+}$ concentration is increased to 2.5 mM. Strips of muscle (approximately 2.5 cm by 1 cm) are removed from the proximal area of the stomach (one from each side) and tied with cotton thread to isotonic transducers under an initial loading tension of 0.35 g.

The preparation is immersed in 20 mls of Krebs solution containing 10$^{-8}$M Devezapide (25µl 2×10$^{-3}$M Devezapide/100% DMF solution in 5 dm$^3$ Krebs) and gassed with 95% O$_2$/5% CO$_2$.

The preparation is washed twice over a 60 minute period then 10 mM KCl is added. At 90 minutes, test compounds (i.e. potential antagonists) are added and a further 60 minute equilibration period allowed. After this time, cumulative agonist (e.g. pentagastrin) dose-response curves are constructed.

The exemplified CCK antagonists were found to be inactive in the gastrin assays up to the limits of solubility, i.e. a concentration of 10$^{-4}$ to 10$^{-5}$M.

We claim:

1. A compound of the formula

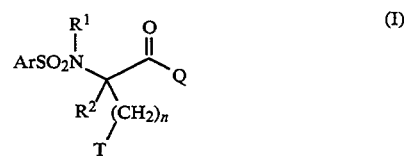

wherein Ar is

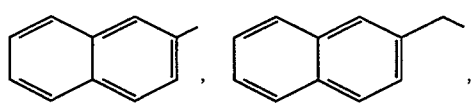

-continued

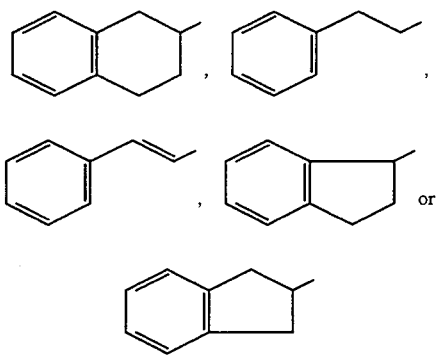

wherein the aromatic moiety may be substituted or unsubstituted, or

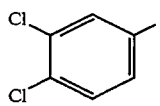

$R^1$ is H, $C_1$ to $C_6$ alkyl, $C_1$ to $C_6$ alkenyl, cycloalkyl, —$(CH_2)_q$aryl or —$(CH_2)_q$(substituted aryl), wherein q is 0 to 4, $R^2$ is H, methyl or ethyl, T is carboxyl, —$CONR^5R^6$, wherein $R^5$ and $R^6$ are independently H or $C_1$ to $C_4$ alkyl, or tetrazolyl, n is 0 to 3, and Q is

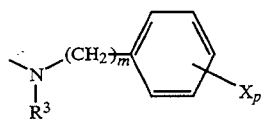

or

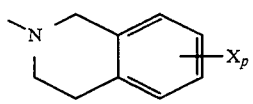

wherein

X is $C_1$ to $C_4$ alkyl, $C_1$ to $C_4$ alkoxy, $C_1$ to $C_4$ thioalkoxy, carboxy, $C_1$ to $C_4$ carboalkoxy, nitro, trihalomethyl, hydroxy, —$NR^7R^8$, (wherein $R^7$ and $R^8$ are independently H or $C_1$ to $C_4$ alkyl, $C_1$ to $C_4$ alkylaryl, $C_1$ to $C_4$ alkyl (substituted aryl, sulfamoyl or halo, m is 1 to 3, p is 0 to 3; and $R^3$ is H, $C_1$ to $C_5$ alkyl or —$(CH_2)_rR^4$ wherein r is 0 to 4 and $R^4$ is aryl or substituted aryl; and pharmaceutically acceptable salts thereof.

2. A compound according to claim 1 wherein Ar is an unsubstituted 2-naphthyl group.

3. A compound according to claim 1 wherein T is carboxyl.

4. A compound according to claim 1 wherein Q is

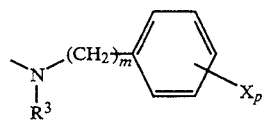

and R, $R^2$ and $R^3$ are all hydrogen.

5. A compound according to claim 4 wherein m is 2.

6. A compound according to claim 1 wherein n is 1.

7. A compound according to claim 1 wherein p is 0 or 1.

8. A compound selected from the group consisting of 2-naphthalenesulphonyl-aspartyl (2-phenethyl)amide, 2-naphthalenesulphonyl-glutamyl (2-phenyl)amide, 2-naphthalenesulphonyl-aspartyl (3-phenylpropyl)amide, derivatives thereof in which the phenyl group is monosubstituted with a chloro or methoxy group, and pharmaceutically acceptable salts thereof.

9. A compound of the formula

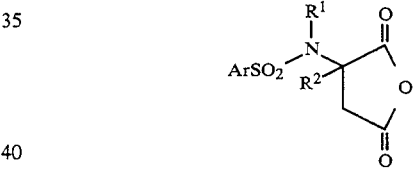

wherein Ar, $R^1$ and $R^2$ are as defined in claim 1.

10. A pharmaceutical composition comprising a compound according to claim 1, together with a pharmaceutically acceptable excipient.

11. A method of reducing cholecystokinin activity in a mammal, comprising the step of administering to a mammal an amount effective for reducing cholecystokinin activity of a compound according to claim 1.

12. A method according to claim 11, wherein, in said compound, T is carboxyl.

* * * * *